(12) United States Patent
Werner et al.

(10) Patent No.: US 6,569,146 B1
(45) Date of Patent: May 27, 2003

(54) METHOD AND APPARATUS FOR TREATING SAPHENOUS VEIN GRAFT LESIONS

(75) Inventors: Dennis Werner, Redmond, WA (US); David H. Dillard, Redmond, WA (US); Ray Fei, Seattle, WA (US); Gary Swinford, Issaquah, WA (US); Verivada Chandru Chandrasekaran, Mercer Island, WA (US); Tim J. Johnson, Seatac, WA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 48 days.

(21) Appl. No.: 09/642,627

(22) Filed: Aug. 18, 2000

(51) Int. Cl.7 .............................................. A61M 31/00
(52) U.S. Cl. ............. 604/509; 604/101.01; 604/101.03; 604/101.05; 604/510; 606/194
(58) Field of Search ................................. 604/508, 509, 604/510, 96.01, 101.01, 101.03, 101.04, 101.05; 606/192, 194

(56) References Cited

U.S. PATENT DOCUMENTS

| | | | |
|---|---|---|---|
| 4,832,688 A | 5/1989 | Sagae et al. | |
| 5,250,060 A | 10/1993 | Carbo et al. | |
| 5,342,306 A * | 8/1994 | Don Michael | 604/101 |
| 5,411,479 A * | 5/1995 | Bodden | 604/98 |
| 5,462,529 A * | 10/1995 | Simpson et al. | 604/101 |
| 5,624,685 A | 4/1997 | Takahashi et al. | |
| 5,665,063 A | 9/1997 | Roth et al. | |
| 5,681,336 A | 10/1997 | Clement et al. | |
| 5,779,673 A * | 7/1998 | Roth et al. | 604/101 |
| 5,836,967 A * | 11/1998 | Schneider | 604/96.01 |
| 5,947,985 A * | 9/1999 | Imran | 604/101 |
| 6,022,336 A * | 2/2000 | Zadno-Azizi et al. | 604/96.01 |

\* cited by examiner

Primary Examiner—Ronald Capossela
(74) Attorney, Agent, or Firm—Kenyon & Kenyon

(57) ABSTRACT

A method for treating loosely formed, friable or fragile lesions in a patient's blood vessel. A catheter having a pair of sealing mechanisms is advanced such that the sealing mechanisms are positioned distal to and proximal to the lesion. The sealing mechanisms are activated to seal the vessel on either side of the lesion. A medication is then delivered through the catheter to the sealed area of the vessel. The medication interacts with the lesion in order to partially or completely solidify it. Once the lesion is solidified, the catheter is removed and the lesion can be treated with a conventional intravascular device.

15 Claims, 2 Drawing Sheets

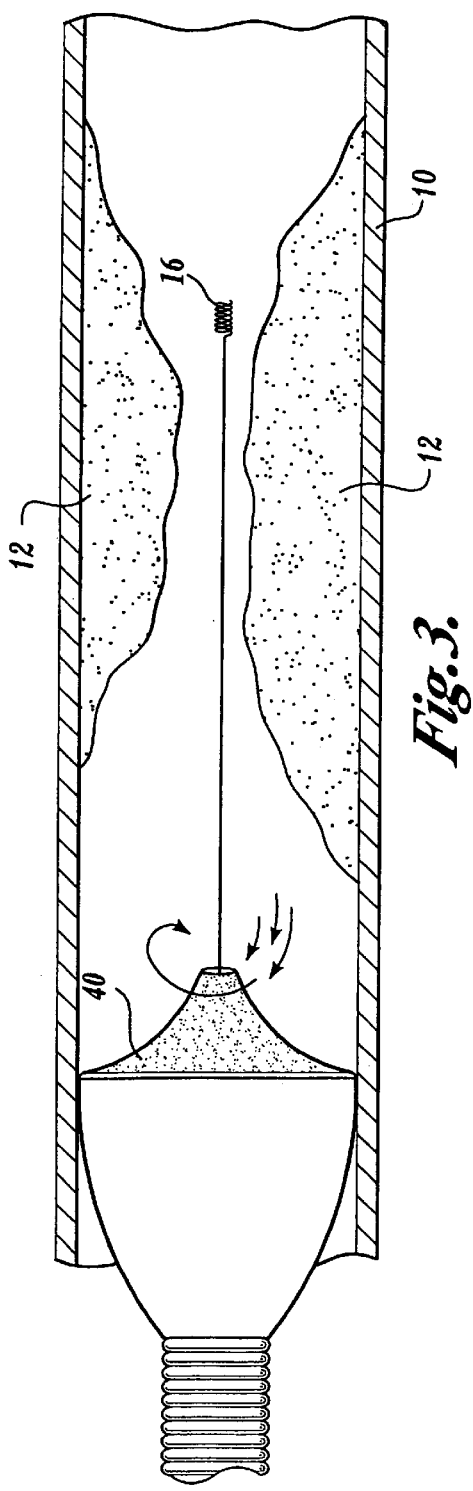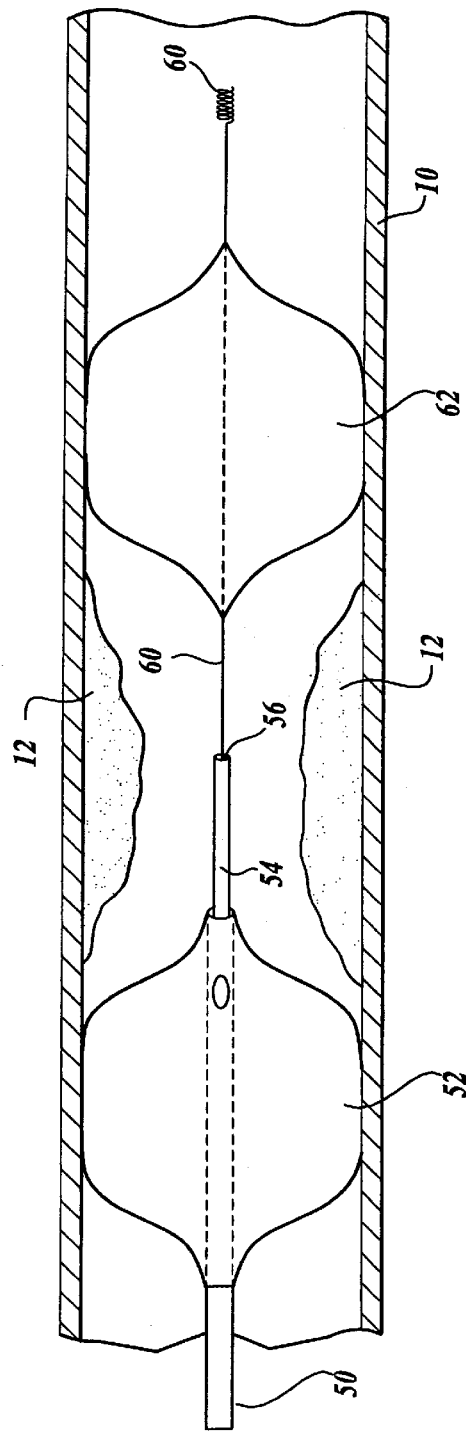

METHOD AND APPARATUS FOR TREATING SAPHENOUS VEIN GRAFT LESIONS

FIELD OF THE INVENTION

The present invention relates to systems for treating vascular lesions and in particular to treating saphenous vein graft lesions (SVGs).

BACKGROUND OF THE INVENTION

One of the most common surgical procedures performed to treat blocked coronary vessels is to bypass the blockage with a vein that is harvested from another portion of a patient's body. The most common veins used are the saphenous veins, which are two large superficial veins of the leg. While this procedure works well to restore blood flow around the heart, it is often the case that these saphenous vein grafts (SVGs) become occluded themselves in a relatively short period of time.

For some physiological reason, which is not completely understood, lesions occurring in an SVG tend to be loosely formed and fragile. These fragile lesions are difficult to treat with conventional intravascular techniques because the lesion may fragment and occlude a vessel further downstream, such as in the brain. Therefore, many patient's must undergo another bypass surgery to restore blood flow to the heart. Given the frequency with which SVGs become occluded, there is a need for a less invasive technique for treating them.

SUMMARY OF THE INVENTION

The present invention is a technique for treating vessels that are occluded with loosely formed, friable lesions such as the type that occur in saphenous vein grafts. To treat a lesion, the lesion is isolated in a vessel and drugs or medications are delivered to the isolated portion of the vessel that solidify the lesion. Once solidified, the lesion can be treated with any number of conventional intravascular surgical techniques such as atherectomy, balloon angioplasty, etc.

In accordance with an embodiment of the invention, one or more inflatable balloons are positioned distal to and proximal from the lesion to be treated. The balloons are inflated to isolate the lesion and an embolizing drug or medication is delivered to the isolated area between the balloons in order to solidify a lesion. Once solidified, the balloons are deflated and removed. Next, the solidified lesion can be treated with a conventional intravascular technique.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 illustrates a solidified lesion formed in accordance with the present invention that is being treated with a conventional intravascular technique; and FIG. 4 illustrates an alternate catheter for sealing a vessel surrounding a lesion to be solidified.

DETAILED DESCRIPTION OF THE PREFERRED EMBODIMENT

Figure 1:
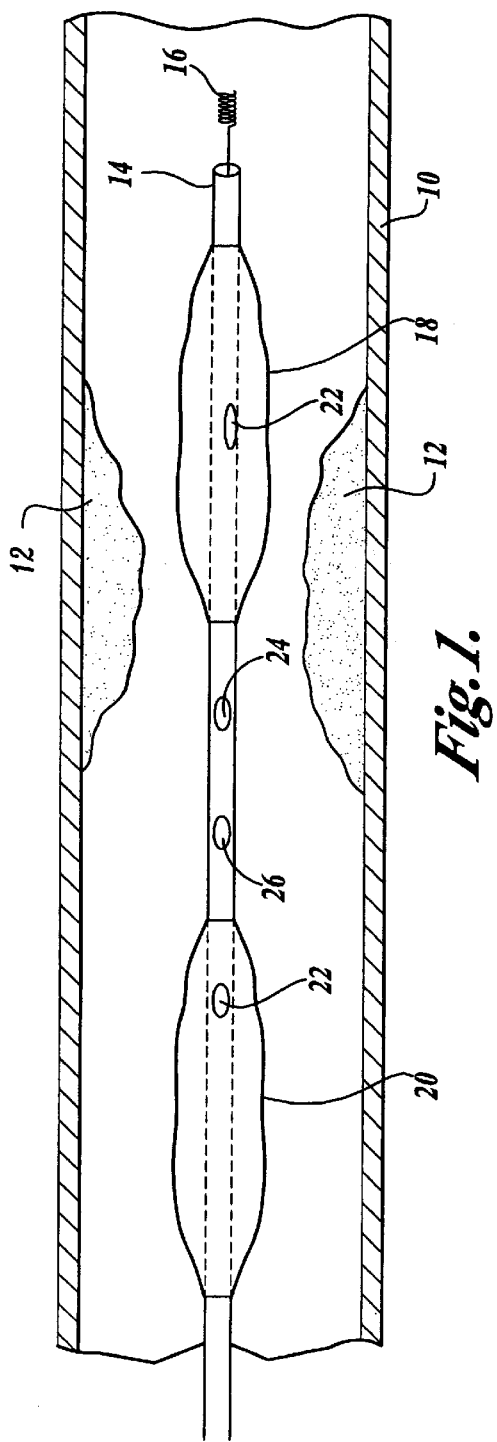
FIG. 1 illustrates a first step of treating a loosely formed, friable vascular lesion with a catheter in accordance with one embodiment of the present invention.

FIG. 1 illustrates a method of treating loosely formed, friable lesions such as those that typically form in a saphenous vein graft (SVG) in accordance with one embodiment of the present invention. A vessel 10 has a lesion 12 within it that partially occludes the vessel. If the vessel 10 is a saphenous vein graft, it is likely that the lesion 12 is fragile. Therefore, the lesion is not easily treated with conventional intravascular techniques such as angioplasty or ablation for fear that the lesion will break up and be carried away by the moving blood flow such that particles of the lesion may become lodged in another vessel downstream. To treat the lesion in accordance with the present invention, a catheter 14 is routed over a conventional guide wire 16. The catheter 14 includes a pair of sealing members that operate to seal the vessel 10 on either side of the lesion 12. In the currently preferred embodiment of the invention, the sealing members comprise a distal balloon 18 and a proximal balloon 20. The catheter 14 includes a lumen (not shown) that terminates at a pair of ports 22 to deliver a fluid such as saline that inflates the distal and proximal balloons in order to seal the vessel.

Figure 2:
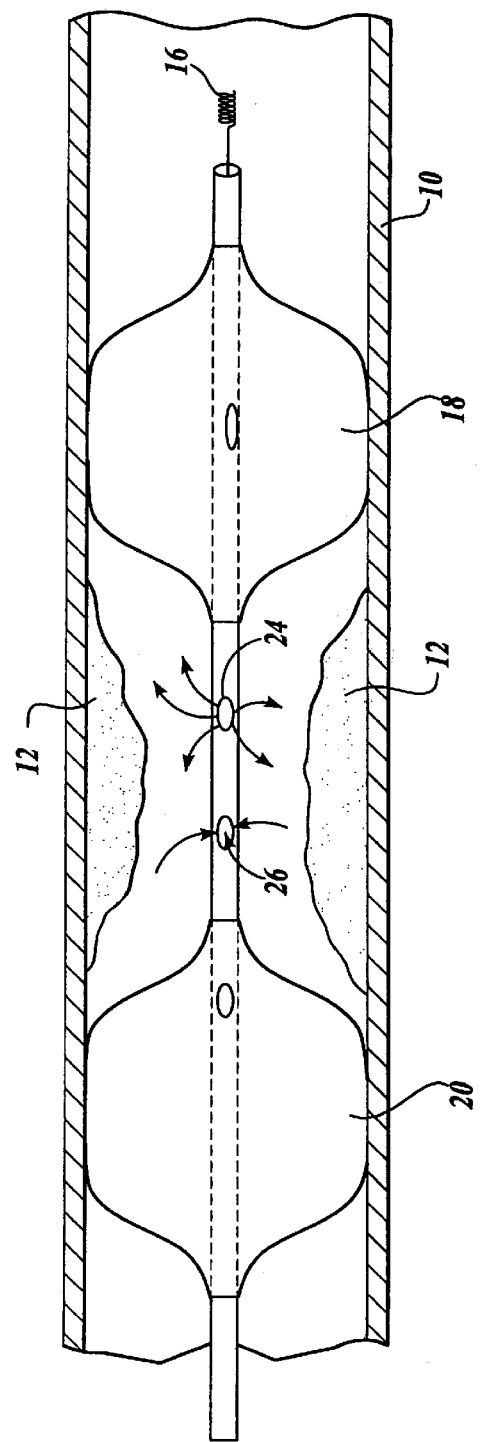
FIG. 2 illustrates a second step in treating a lesion in accordance with the present invention.

As illustrated in FIG. 2, once the distal balloon 18 and proximal balloon 20 are inflated, the lesion 12 is substantially isolated between the two balloons 18 and 20. A drug or medication is then delivered through another lumen within the catheter 14 that terminates at a port 24 that is between the two balloons 18, 20. Once the drug or medication is expelled through the port 24, it acts to solidify the lesion 12. In the presently preferred embodiment of the invention, the drug or medication includes thrombin, fibrinogen or other chemical compounds having the ability to partially or completely solidify the lesion 12. In order to maintain pressure within the vessel as the drug or medication is being delivered, the catheter 14 also includes another lumen that terminates at a port 26 that is between the balloons 18 and 20. Preferably, fluid is withdrawn from the vessel through the port 26 at or near the rate of which fluid containing the drug or medication is delivered to the sealed area of the vessel through the port 24.

Once the drug or medication has been delivered to the lesion and a sufficient period of time has elapsed to solidify the lesion, the distal balloon 18 and proximal balloon 20 are deflated and the catheter is withdrawn from the vessel. As shown in FIG. 3, once the lesion 12 has been solidified within the vessel 10, a conventional intravascular apparatus such as an ablation burr 40 can be routed over the guide wire 16 in order to remove the solidified lesion from the patient's vessel.

FIG. 4 illustrates an alternative mechanism for isolating a loosely formed, friable lesion and solidifying it. A catheter 50 has a sealing mechanism such as a balloon 52 disposed at its distal end. Routed through the catheter 50 is second catheter 54 having an opening 56 at its distal end. Routed through the catheter 54 is a guidewire 60 having a sealing mechanism 62 such as a balloon 62 disposed near its distal end. A suitable guidewire having a guidewire inflatable balloon is the PercuSurge Guardwire™ available from PercuSurge, Inc.

In operation, the catheter 50 is positioned proximal to the lesion 12 and the guidewire 60 having the sealing mechanism 62 is positioned distal to the lesion 12. The sealing mechanisms 52 and 62 are inflated to isolate the lesion 12 within the vessel 10. Next, a drug or medication such as thrombin is injected out the distal end 56 of the catheter 54. Once an amount of thrombin has been injected that would fill up the space between the sealing mechanisms 52 and 62, a drug or medication such as fibrinogen is injected out the distal end 56 of the catheter 54. As the fibrinogen is injected, the, catheter 54 is retracted back slowly allowing adequate coverage within the isolated area. The fibrinogen is injected until an adequate amount fills the isolated area. By then, the catheter 54 should be positioned within the catheter 50. The thrombin and fibrinogen are given about thirty seconds to set up a fibrin lesion. The lesion can then be treated with conventional intravascular techniques.

In a similar embodiment, saline is injected through the catheter 54 and aspirated out the catheter 50, thus washing the loosely formed, friable lesion material. The remaining material not removed is treated with a conventional intravascular technique.

In yet another embodiment, a foaming agent may be used in connection with the drugs or medication to solidify the lesion 12 within the sealed portion of the vessel 10.

As can be seen, the present invention is a method for treating loosely formed, friable or fragile lesions by sealing the area in which the lesion is located and applying a medication to solidify the lesion. The present invention is not limited to treating lesions in saphenous vein grafts but could be used in substantially any vessel where fragile or loosely formed, friable lesions may form. Furthermore, once the lesion has been solidified, it may not be necessary to remove it if the lesion does not restrict too much blood from flowing in the surrounding vessel.

While the preferred embodiment of the invention has been illustrated and described, it will be appreciated that various changes can be made therein without departing from the scope of the invention. It is therefore intended that the scope of the invention be determined from the following claims and equivalents thereto.

The embodiments of the invention in which an exclusive property or privilege is claimed are defined as follows:

1. A system for treating lesions, comprising:
   a catheter with a pair of sealing mechanisms disposed thereon such that the sealing mechanisms can be positioned distal to and proximal from a lesion and deployed to isolate the lesion within a vessel;
   a port on the catheter between the sealing mechanisms through which a medication is delivered, the medication acting to substantially solidify the lesion within the vessel; and
   a guide wire over which the catheter is routed to the lesion.

2. The system of claim 1, wherein the pair of sealing mechanisms are inflatable balloons.

3. The system of claim 1, further comprising:
   a second port on the catheter located between the pair of sealing mechanisms for removing a volume liquid from the sealed portion of the vessel that is substantially equal to a volume of the medication delivered.

4. A system for treating loosely formed, friable lesions in a vessel, comprising:
   a pair of sealing mechanisms that are positionable proximal to and distal to a lesion in order to isolate an area including the lesion in a vessel;
   a catheter for delivering a drug or medication to the isolated area in order to at least partially solidify the lesion.

5. The system of claim 1, wherein the pair of sealing mechanisms comprise a first and second balloon.

6. The system of claim 5, wherein the first and second balloon are on a single catheter.

7. The system of claim 5, wherein the first balloon is on a catheter and the second balloon is on a guidewire that passes through the catheter.

8. The system of claim 4, further comprising an atherectomy device for removing or compressing the at least partially solidified lesion.

9. A method of treating lesions comprising:
   advancing a catheter having a pair of sealing mechanisms in a vessel such that the pair of sealing mechanisms are positioned distal to and proximal from a lesion;
   deploying the pair of sealing mechanism such that the lesion is isolated within the vessel;
   delivering a medication to the isolated lesion such that the lesion becomes more solid;
   removing the catheter from the vessel; and
   removing the solidified lesion.

10. The method of claim 9, wherein the lesion is removed by an intravascular device.

11. The method of claim 9, wherein the lesion is removed by aspiration.

12. The method of claim 9, wherein the lesion is removed by angioplasty.

13. A system for treating lesions, comprising:
    a pair of sealing mechanisms that are positionable proximal to and distal to a lesion in a vessel in order to isolate the lesion within the vessel;
    means for delivering a medication to the lesion for partially or completely solidifying the lesion, said means including a catheter with a port on the catheter between the sealing mechanisms through which the medication is delivered.

14. The system of claim 13, wherein the sealing mechanisms are inflatable balloons.

15. The system of claim 13, further comprising:
    a second port on the catheter located between the pair of sealing mechanisms for removing a volume liquid from the sealed portion of the vessel that is substantially equal to a volume of the medication delivered.

* * * * *